(12) United States Patent
Herron et al.

(10) Patent No.: US 9,329,122 B2
(45) Date of Patent: May 3, 2016

(54) DIFFUSE REFLECTANCE INFRARED FOURIER TRANSFORM SPECTROSCOPY FOR CHARACTERIZATION OF EARTH MATERIALS

(75) Inventors: Michael M. Herron, Ridgefield, CT (US); Susan Herron, Ridgefield, CT (US); Alyssa Charsky, Sudbury, MA (US); Ridvan Akkurt, Lexington, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 757 days.

(21) Appl. No.: 13/571,741

(22) Filed: Aug. 10, 2012

(65) Prior Publication Data
US 2013/0046469 A1 Feb. 21, 2013

Related U.S. Application Data

(60) Provisional application No. 61/523,650, filed on Aug. 15, 2011.

(51) Int. Cl.
*G01V 8/00* (2006.01)
*G01N 21/3563* (2014.01)
*G01N 21/35* (2014.01)

(52) U.S. Cl.
CPC .... *G01N 21/3563* (2013.01); *G01N 2021/3595* (2013.01)

(58) Field of Classification Search
CPC .................. G01N 2021/3595; G01N 21/3563; G01N 1/286; G01N 23/20; G01N 33/24
See application file for complete search history.

(56) References Cited

U.S. PATENT DOCUMENTS

| | | | |
|---|---|---|---|
| 4,510,573 A | 4/1985 | Boyce et al. | |
| 4,839,516 A | 6/1989 | Freeman et al. | |
| 5,161,409 A | 11/1992 | Hughes et al. | |
| 5,360,738 A * | 11/1994 | Jones et al. | 436/30 |
| 5,557,103 A * | 9/1996 | Hughes et al. | 250/255 |
| 5,741,707 A | 4/1998 | Herron et al. | |
| 7,781,729 B2 | 8/2010 | Wang et al. | |
| 8,367,419 B2 * | 2/2013 | Li et al. | 436/107 |
| 2010/0080351 A1 | 4/2010 | Hession-Kunz et al. | |

FOREIGN PATENT DOCUMENTS

AU 2010202654 A1 1/2011

OTHER PUBLICATIONS

Breen, "Bulk mineralogical characterization of oilfield reservoir rocks and sandstones using Diffuse Reflectance Infrared Fourier Transform Spectroscopy and Partial Least Squares analysis", Journal of Petroleum Science and Engineering, vol. 60(1), Jan. 2008, pp. 1-17.
Herron, et al., "Dual-Range FT-IR Mineralogy and the Analysis of Sedimentary Formations", International Symposium of the Society of Core Analysts, No. 9729, 1997, 11 pages.

(Continued)

*Primary Examiner* — Elias Desta (57) ABSTRACT

The subject disclosure relates to the evaluation of lithology, mineralogy and organic content of earth materials. More particularly, the subject disclosure relates to evaluating lithology, mineralogy and organic content of earth materials using diffuse reflectance infrared Fourier transform spectroscopy (DRIFTS).

21 Claims, 9 Drawing Sheets

(56) References Cited

OTHER PUBLICATIONS

Herron, Michael M., "Geochemical classification of terrigenous sands and shales from core or log data", Journal of Sedimentary Research, vol. 58(5), Sep. 1988, pp. 820-829.

Kenna, et al., "Evaluation and calibration of a Field Portable X-Ray Fluorescence spectrometer for quantitative analysis of siliciclastic soils and sediments", Journal of Analytical Atomic Spectrometry, vol. 26 (2), 2011, pp. 395-405.

Kramer, Richard, "Chemometric Techniques for quantitative analysis", Marcel Dekker, Inc., New York, 1998, 203 pages.

Matteson, et al., "Quantitative mineral analysis by Fourier Transform Infrared Spectroscopy", Society of Core Analysts Annual Meeting, Paper No. 9308, 1993, pp. 1-15.

Vogel, et al., "Fourier transform infrared spectroscopy, a new cost-effective tool for quantitative analysis of biogeochemical properties in long sediment records", Journal of Paleolimnology, vol. 40, 2008, pp. 689-702.

Linker Raphael (2011). Application of FTIR Spectroscopy to Agricultural Soils Analysis, Fourier Transforms—New Analytical Approaches and FTIR Strategies, Prof. Goran Nikolic (Ed.), ISBN: 978-953-307-232-6, InTech, DOI: 10.5772/15732. Available from: http://www.intechopen.com/books/fourier-transforms-new-analytical-approaches-and-ftir-strategies/application-of-ftir-spectroscopy-to-agricultural-soils-analysis.

He, Yong et al. "Measurement and Analysis of Soil Nitrogen and Organic Matter Content Using near-Infrared Spectroscopy Techniques." Journal of Zhejiang University. Science. B 6.11 (2005): 1081-1086. PMC. Available from: http://www.ncbi.nlm.nih.gov/pmc/articles/PMC1390655/.

Patent Examination Report No. 2 issued in related AU Application No. 2012295114 mailed Dec. 7, 2015.

* cited by examiner

DIFFUSE REFLECTANCE INFRARED FOURIER TRANSFORM SPECTROSCOPY FOR CHARACTERIZATION OF EARTH MATERIALS

CROSS-REFERENCE TO RELATED APPLICATION

This application claims the benefit of U.S. Provisional Patent Application Ser. No. 61/523,650 filed Aug. 15, 2011, which is incorporated herein by reference in its entirety.

FIELD

This patent specification generally relates to the evaluation of lithology, mineralogy and organic content of earth materials. More particularly, the subject disclosure relates to evaluating lithology, mineralogy and organic content of earth materials using diffuse reflectance infrared Fourier transform spectroscopy (DRIFTS).

BACKGROUND

The subject disclosure relates to evaluation of mineralogy and organic content of earth materials. The mineralogy of an earth formation surrounding a borehole is valuable to determining whether it is feasible and cost efficient to produce hydrocarbons from the borehole in question.

There are a number of techniques in the oil industry to perform quantitative mineral analysis of an earth formation. In each case, core samples are extracted from the borehole and are used to represent the formation at different depths.

Infrared spectroscopy, particularly Fourier transform infrared (FTIR) spectroscopy, has been used to analyze the mineral composition of rock samples. Typically, a portion of the core sample is ground up and added to a carrier such as potassium bromide (KBr). The mixture is then formed into a pellet through a series of grinding and dispersing steps. The pellet is pressed and weighed to account for lost material. Finally, the pellets are irradiated with infrared radiation in an FTIR spectrometer and a spectral response signal is obtained representative of the infrared radiation absorbed by the sample. The frequency and amplitude of each characteristic spectral response can be obtained. Comparison is made in the spectrum for the sample with spectra for standard minerals to determine a quantitative measure of the minerals in each sample. Many of the approaches in transmission FT-IR are used in the subject disclosure with reflection FT-IR, including the analysis of whole and powdered mineral standards that have been chemically assayed for purity.

X-ray fluorescence (XRF) spectrometers have been used to analyze the chemical composition of rock samples. In X-ray fluorescence (XRF) spectrometers, the chemical composition of a substance is determined by irradiating the sample under test with X-rays and by recording the secondary X-ray fluorescent radiation emitted by the sample.

Handheld X-ray fluorescence (XRF) analyzers are commercially available from many companies. These analyzers are calibrated for some specific applications, but they appear to need calibration/optimization in order to provide robust measurements for common sedimentary earth materials; an example of how this calibration may be performed is provided by Kenna et al., entitled "Evaluation and calibration of a field portable X-ray fluorescence spectrometer for quantitative analysis of siliciclastic soils sediments," Journal of Analytical Atomic Spectrometry, 2010. Such analyzers have been incorporated into core scanning systems, for example, the GEOTEK multi-sensor core logger.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In accordance with some embodiments, a method of analyzing an earth sample is provided. The method comprises irradiating the earth sample with infrared energy and collecting one or more spectra of the infrared energy reflected from the earth sample. The method further comprises creating a dataset and analyzing the dataset by performing regression analysis against a library of data obtained from standard spectra. Finally, the method comprises characterizing the earth sample from results obtained by the regression analysis.

In accordance with some other embodiments, an apparatus for analyzing an earth sample is disclosed. The apparatus comprises an infrared light source for generating infrared energy at a plurality of wavelengths, a detector for detecting infrared energy that is reflected by the earth sample and an analyzer for analyzing the reflected energy by performing regression analysis against a library of data obtained from standard spectra. The apparatus further comprises determining lithology, mineralogy and organic content of the earth sample from results obtained by the regression analysis.

In accordance with some embodiments, a method of characterizing an earth material using diffuse reflectance infrared Fourier transform spectroscopy (DRIFTS) is disclosed. The method comprises irradiating the earth material with infrared energy over a spectrum of wavelengths; collecting one or more spectra of the infrared energy reflected from the earth material over the spectrum of wavelengths; performing processing at one or more wavelengths comprising the one or more infrared spectra; comparing results of the processing with one or more libraries of standard spectra; and identifying the lithology and mineralogy based on a similarity of the results of the processing at one or more wavelengths with the libraries of standard spectra.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein.

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

Embodiments of the subject disclosure relate to core and cuttings analysis, mineral analysis and interpretation of lithology and mineralogy from diffuse reflectance infrared Fourier transform spectroscopy (DRIFTS) and chemistry measurements.

Embodiments of the subject disclosure relate to methods of using diffuse reflectance infrared Fourier transform spectroscopy (DRIFTS). Reflection Fourier transform infrared spectra are taken of earth samples with little or no sample preparation and interpreted in terms of lithology, mineralogy and organic content. Organic content is further interpreted in terms of types of hydrocarbon bonds which leads to interpretation as kerogen, bitumen etc. The organic content is then characterized in terms of hydrocarbon bond types such as C—H and C—$H_2$ etc. The processing involves a weighted least squares comparison of the measured sample spectrum with a library of standard mineral and hydrocarbon spectra rather than simple peak height or area analysis.

In further embodiments, the methods disclosed above are used on well cuttings which have been cleaned of mud coatings and crushed. The drilling mud is first removed and the samples are conditioned for optimal interpretation in terms of mineralogy, lithology and kerogen content. In non-limiting examples, this may include removal of any hydrocarbon-bearing mud or mud additives and a reduction of particle size for a more accurate analysis. Various cleaning methods may be used, in a non-limiting example, a toluene solvent is used. In non-limiting examples, the cuttings are crushed to a particle size of less than 200 microns but other particle sizes are contemplated. In further embodiments, simple reflection FT-IR is used on core material with no crushing.

In further embodiments, reflection Fourier transform infrared measurements are used in combination with X-ray fluorescence (XRF) measurements to provide chemical concentrations of the samples. In non-limiting examples, chemistry measurements may be used to provide quality control for the lithology/mineralogy and/or to refine the answers.

In one embodiment, the tool system capable of making these measurements comprises an x-ray fluorescence spectroscopy tool such as described in U.S. Pat. No. 4,510,573 to Boyce et al. which is hereby incorporated by reference herein in its entirety. Alternatively, the X-ray fluorescence spectroscopy tool may be a currently available hand-held type X-ray fluorescence spectroscopy instrument which is suitably adapted for use in a borehole.

In further embodiments, reflection Fourier transform infrared measurements are used in combination with X-ray diffraction (XRD) measurements which provide complementary information on the lithology and mineralogy constituents present in the samples. The XRD data may be used to identify mineral phases present and exclude possible mineral phases in order to improve the accuracy of the reflection FT-IR interpretation.

Reflection Fourier transform infrared spectroscopy is a relatively new technology that has been used in the art world and for currency evaluation. Reflection Fourier transform infrared spectroscopy use in earth materials has been restricted to a very few attempts to identify mineralogy from samples with extensive sample preparation with KBr (See Breen et al., "Bulk mineralogical characterization of oilfield reservoir rocks and sandstones using Diffuse Reflectance Infrared Fourier Transform Spectroscopy and Partial Least Squares analysis," Journal of Petroleum Science and Engineering, Volume 60, Issue 1, January 2008, Pages 1-17) and to identification of kerogen.

In embodiments of the subject disclosure no KBr is used and little to no sample preparation of earth materials is needed. In non-limiting examples, these earth materials may be core, cuttings or outcrop. In general, the subject disclosure is directed to analysis of samples obtained from earth materials in connection with oil and gas exploration and production. The earth samples are taken from boreholes in the earth, and may be taken from oil or gas producing formations or from exploratory wells. Lithology (mineral group) abundances, and/or mineral abundances are determined from a comparison of the reflection spectrum with a library of standard spectra using one or more interpretation techniques that may include multiple linear regression, weighted least squares regression with the weights determined to optimize the mineralogy, or partial least squares regression (see for example Kramer, entitled "Chemometric Techniques for quantitative analysis," 1998). Hydrocarbon content and typing is determined at the same time as the lithology/mineralogy spectrum and involves assessing the overlapping part of the spectrum shared by hydrocarbons and certain minerals.

In embodiments, the reflection FTIR data may be used alone to provide formation mineralogy. Alternatively, XRF measurements can be made using, in one non-limiting example, a portable XRF gun to obtain the chemical composition of the samples. The chemical composition may be used in combination with the reflection FTIR data.

Figure 1:
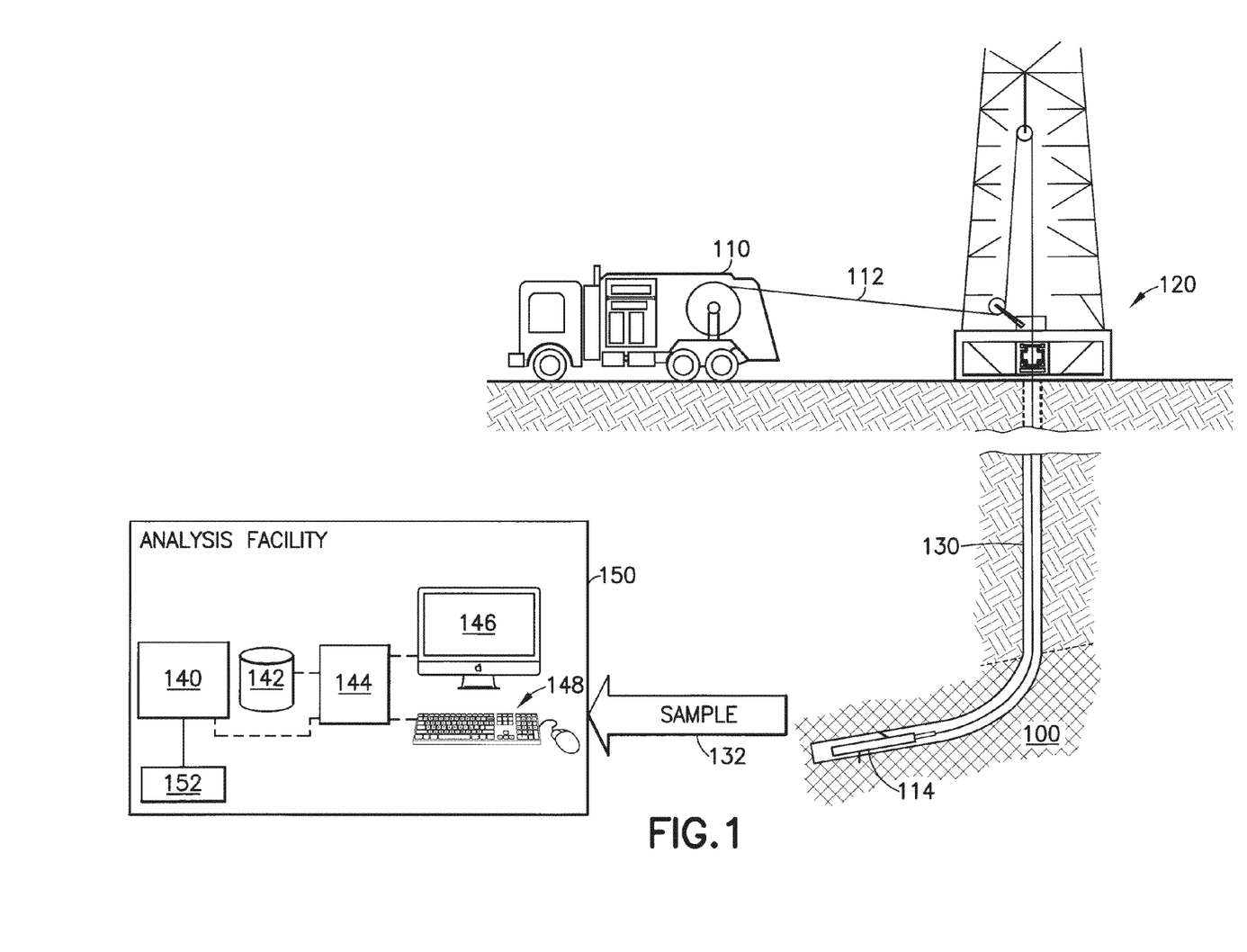
FIG. 1 shows a sampling tool being deployed in a wellbore and an analysis facility, according to some embodiments.

FIG. 1 shows a sampling tool being deployed in a wellbore and an analysis facility, according to some embodiments. In a non-limiting example the sampling tool is a core sampling tool. Wireline truck (110) is deploying wireline cable (112) into well (130) via well head (120). Wireline tool (114) is disposed on the end of the cable (112) in an unconventional subterranean formation (100). According to some embodiments, formation (100) is an unconventional reservoir, such as a hydrocarbon bearing shale reservoir. Tool (114) includes a sampling tool as shown, in a non-limiting example, a core sampling tool. Although a wireline sampling tool is shown, according to other embodiments, other types of sampling tools are used such as while drilling and/or coiled tubing conveyed tools. Samples (132) are from an unconventional rock formation (100) and are retrieved at the surface from the tool (114) and transported to an analysis facility (150). Note that the analysis facility (150) can be located at the wellsite (which can be onshore or offshore) or it can be located remotely from the wellsite. Facility (150) includes a Fourier transform spectrometer (152), one or more central processing units (140), storage system (142), communications and input/output modules (140), a user display (146) and a user input system (148). Storage system (142) can be in the form of magnetic storage, such as a hard disk, and/or in the form of solid-state memory such as flash memory, but is not limited to these two. Input/output modules (140) include modules to communicate with and control the Fourier transform spectrometer (152). Analysis facility (150) may also include an x-ray fluorescence (XRF) device, an x-ray diffraction (XRD) device or other apparatuses as known to those skilled in the art for characterizing rock samples.

Figure 2:
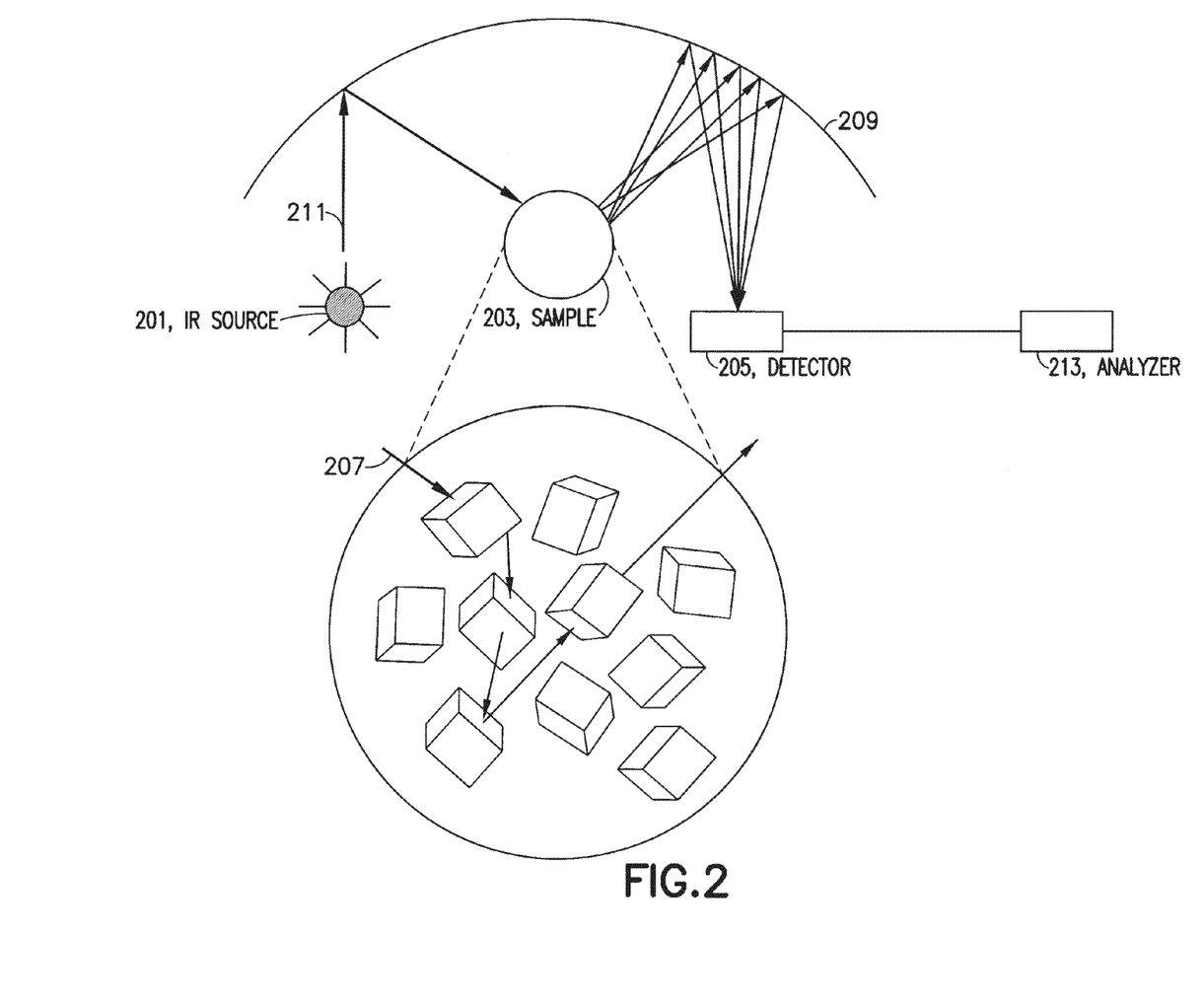
FIG. 2 shows the general mechanisms of diffuse reflectance infrared Fourier transform spectroscopy (DRIFTS)

FIG. 2 depicts the general mechanism of diffuse reflectance infrared Fourier transform spectroscopy (DRIFTS). DRIFTS responds to the modes of molecular vibrations of the components of the sample. In a non-limiting example, DRIFTS provides an easy and rapid measurement of drill cuttings, which can be analyzed for the mineralogy and kerogen content of reservoir rocks. As depicted in FIG. 2, source (201) is a source of infrared radiation. Source (201) emits radiation beam (211) which is directed to spherical mirror (209) which, in turn, directs source (201) to sample (203). When the infrared light source (201) is directed at a sample (203), the infrared (IR) beam (207) is specularly reflected, diffusely reflected, or transmitted through part of the sample. The reflected energy is captured by spherical mirror (209) and reflected down to detector (205). A detector (205) then collects the diffusely reflected light which is measured as a function of wavenumber. Each fundamental molecular vibration corresponds to a specific absorbance band, therefore, the sample components can be extracted by analyzing the DRIFTS spectrum.

An analyzer (213) then performs a Fourier transformation on the captured data of the reflected energy in order to determine the presence or absence of compounds. An analyzer (213) is suitably a conventional computer with the necessary software.

Figure 3:
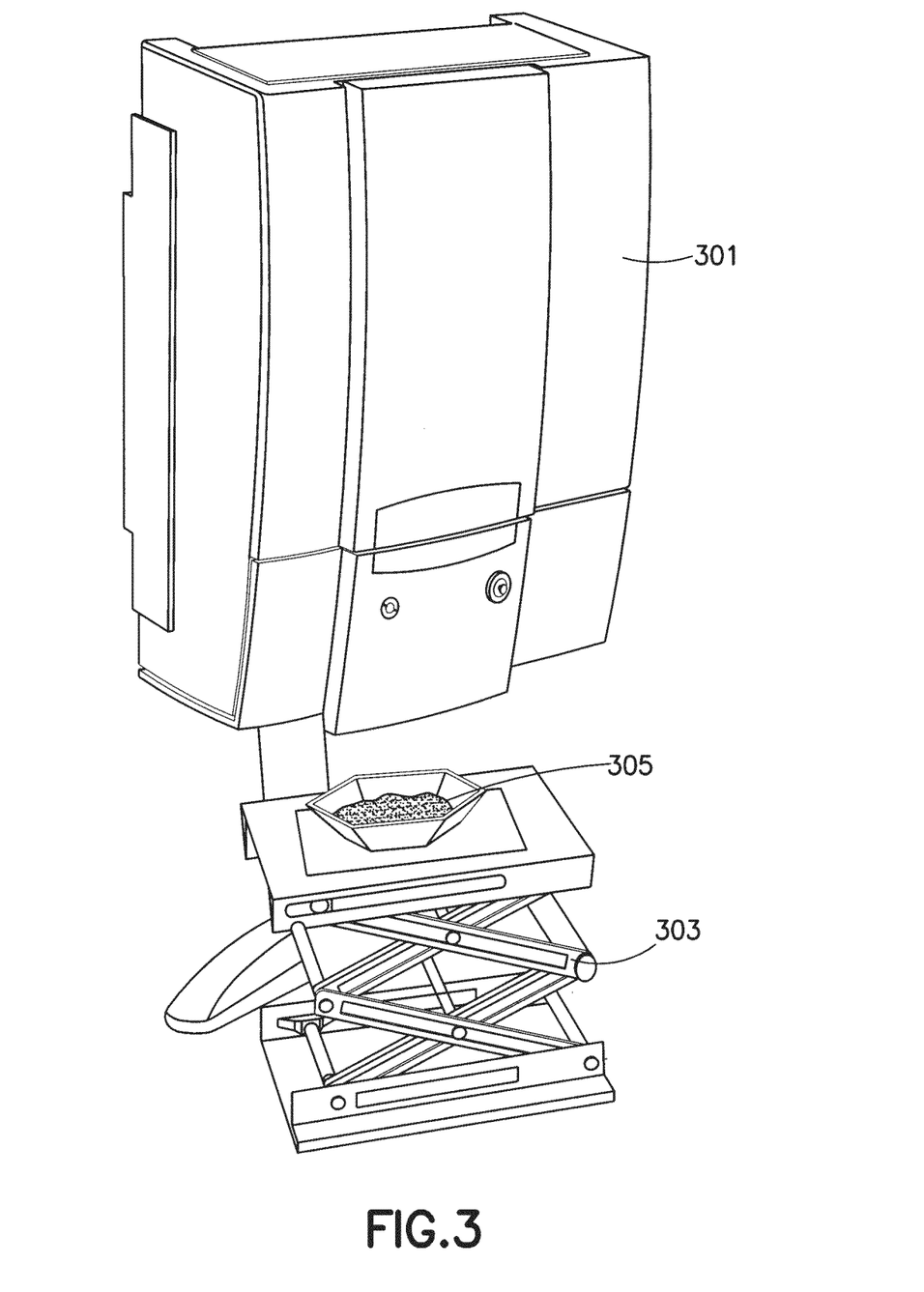
FIG. 3 illustrates a spectrometer according to embodiments of the subject disclosure.

FIG. 3 depicts a spectrometer (301) according to embodiments of the subject disclosure. In non-limiting examples, the spectrometer which may be used is a Bruker Optics Alpha-R spectrometer. The spectrometer is mounted vertically on a movable arm so that the infrared light shines down onto the sample (305) positioned on a movable stage (303) at an optimal distance from the source. In non-limiting embodiments, samples were scanned at 4 cm$^{-1}$ resolution over the mid infrared range 375-4000 cm$^{-1}$.

In one non-limiting example, DRIFTS spectra can be analyzed to more accurately quantify mineralogy and kerogen content of shale cuttings using a least squares regression and minimal sample preparation.

Before being analyzed for mineralogy and kerogen by DRIFTS, cuttings drilled with oil based mud (OBM) have the mud removed from the surface of the cuttings. The OBM contains organic base oil and both organic and inorganic mud additives, which will contribute to the DRIFTS spectrum and interfere with the accuracy of the mineralogy and kerogen measurements. After removal of the OBM, the cuttings are reduced in particle size to reduce spectra effects.

Figure 4A:
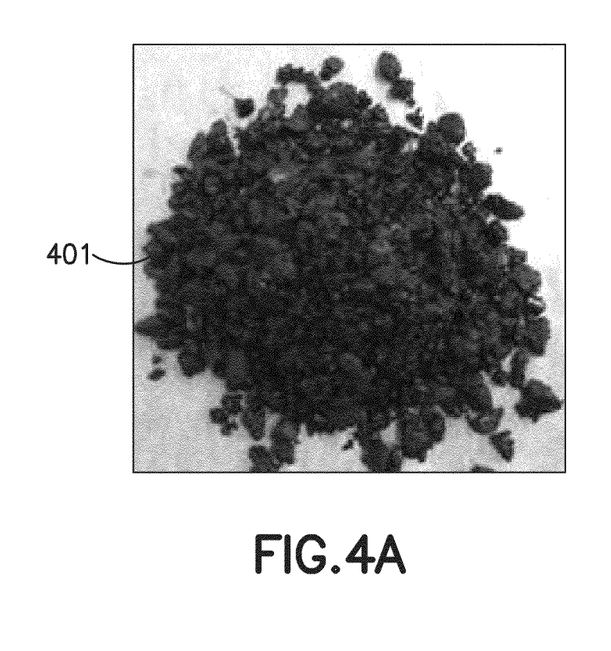
FIG. 4A illustrates cuttings as received from the well site and FIG. 4B illustrates the same cuttings after cleaning and particle size reduction.
Figure 4B:
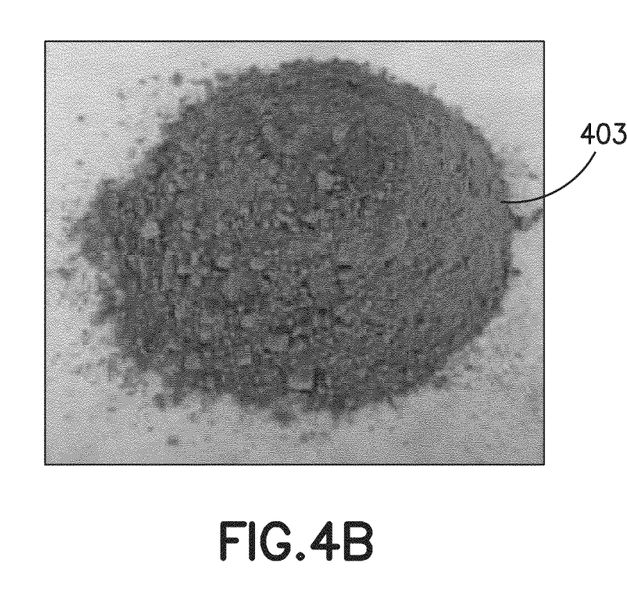

FIG. 4A illustrates cuttings (401) as received from the well site, and FIG. 4B illustrates the same cuttings (403) after cleaning and particle size reduction. The cuttings were cleaned with diesel, rinsed with pentane, crushed to a particle size of less than 200 microns and finally rinsed again with pentane. The minimum sample amount is approximately 1 g of sample. To quantitatively measure samples with the minimum amount of preparation possible, in non limiting examples, the common practice of dilution of the sample with potassium bromide (KBr) is not used. For each sample, a plurality of scans were collected and then averaged to give the resultant DRIFTS spectrum. Spectra were collected in Kubelka-Munk intensity.

Embodiments disclose using the Kubelka-Munk conversion of spectra and a least squares regression analysis. DRIFTS spectra can be analyzed for mineralogy to an average error of ±2.1% and kerogen to ±0.7 wt % for well samples. DRIFTS is sensitive to the changes in lithology and kerogen content over the length of a well and therefore can be used to identify formation tops and pay zones. The ability to both accurately measure both mineralogy and kerogen content rapidly on cutting samples, with little sample preparation, where there may otherwise be little well data, is advantageous.

The Kubelka-Munk function (See Vogel et al., "Fourier transform infrared spectroscopy, a new cost-effective tool for quantitative analysis of biogeochemical properties in long sediment records," Journal of Paleolimnology (2008) 40, 689-702) is a theory, which relates the concentration of the absorbing species in Kubelka-Munk intensity, KM, to the reflectance, R, of the sample:

$$KM=(1-R)^2/2R \quad (1)$$

By making this conversion to Kubelka-Munk intensity, rather than collecting the spectra in absorbance units, the spectra exhibit improved linearity as described by the Beer-Lambert law (See Miller et al. "Beer-Lambert Law," VDM Publishing House Ltd., Saarbrüken (2009), 154p) relating concentration, c, to absorbance, A:

$$A=\epsilon lc \quad (2)$$

Where $\epsilon$ is the molar absorptivity of the sample and l is the absorption path length. By assuming DRIFTS spectra obey the Beer-Lambert Law when collected as Kubelka-Munk spectra at every wavelength, the mineralogy and kerogen content can be extracted from the spectrum by solving for the sample components as a linear combination of known standard minerals. A library of mineral standard spectra was built by collecting spectra of mineral species known to be chemically pure as measured by X-Ray Fluorescence (XRF) which may be stored in storage system (152). Mineral standards in the library include calcite, dolomite, illite, smectite and kaolinite. This list of mineral standards is not an exhaustive list and as such other mineral standards may be included. Additionally, kerogen spectra were collected from dimineralized rocks, and added to the library as standard organic spectra. Although other organic components may be present in rocks, including bitumen, organic components of the samples which have an aliphatic C—H band are referred to as kerogen. Using the standard library, a sample of unknown composition may be solved for its constituents by assuming the samples spectrum is a linear combination of each standard spectrum times its concentration in the sample. This is accomplished by using a least squares regression to solve for the mineral and kerogen concentrations.

Experiments were carried out to evaluate the least-squares regression to solve quantitatively for individual minerals from DRIFTS spectra using artificial mineral mixtures consisting of two components each. For each two component combination of calcite, illite, quartz, dolomite and kaolinite, mixtures were made in differing proportions e.g., 10:90, 20:80, 30:70, 50:50, 70:30, 80:20, and 90:10. The components were weighed and homogenized. A DRIFTS spectrum was then collected of the homogenized mixture. A least squares regression was run on the artificial binary mixtures to solve for the components. To quantitatively evaluate the accuracy and precision of the least squares regression, the calculated mineralogy values are compared to the known concentrations. The average absolute difference in weight percent between known concentration and measured by DRIFTS for the binary artificial mixtures varied from about 2% for Calcite to about 4% for Kaolinite with Illite, Quartz and Dolomite having about a 3.5% difference.

In further experiments, cuttings samples were prepared for DRIFTS measurements as described above. A DRIFTS spectrum was collected for each cutting depth interval and analyzed for mineralogy and kerogen. The mineralogy values acquired from the DRIFTS analysis were compared to mineralogy values as measured on a split of the sample by dual-range Fourier transform spectroscopy (DRFT-IR) analysis, which has been shown to accurately measure mineralogy to within an error of ±2 wt %. See Matteson et al., "Quantitative mineral analysis by Fourier Transform Infrared Spectroscopy," paper 9308 presented at the 1993 Society of Core Analysts Annual Meeting, August 9-11, 15p and Herron et al., "Dual-Range FT-IR Mineralogy and the Analysis of Sedimentary Formations," paper 9729 presented at the International Symposium of the Society of Core Analysts, September 7-10, 12p, the contents of both are herein incorporated by reference. Kerogen values obtained by DRIFTS were compared to total organic carbon (TOC) values independently measured by SGS Laboratories™ in Canada by LECO®. The average absolute difference between DRFT-IR mineralogy and DRIFTS mineralogy were below 3% for carbonate, clay, quartz and kaolinite. To approximate kerogen from total organic content (TOC), the TOC value is multiplied by the commonly used factor of 1.2 to account for the non-carbon portion of the kerogen by other elements such as hydrogen. The DRIFTS kerogen values match very closely to the 1.2*TOC from LECO.

Figure 5:
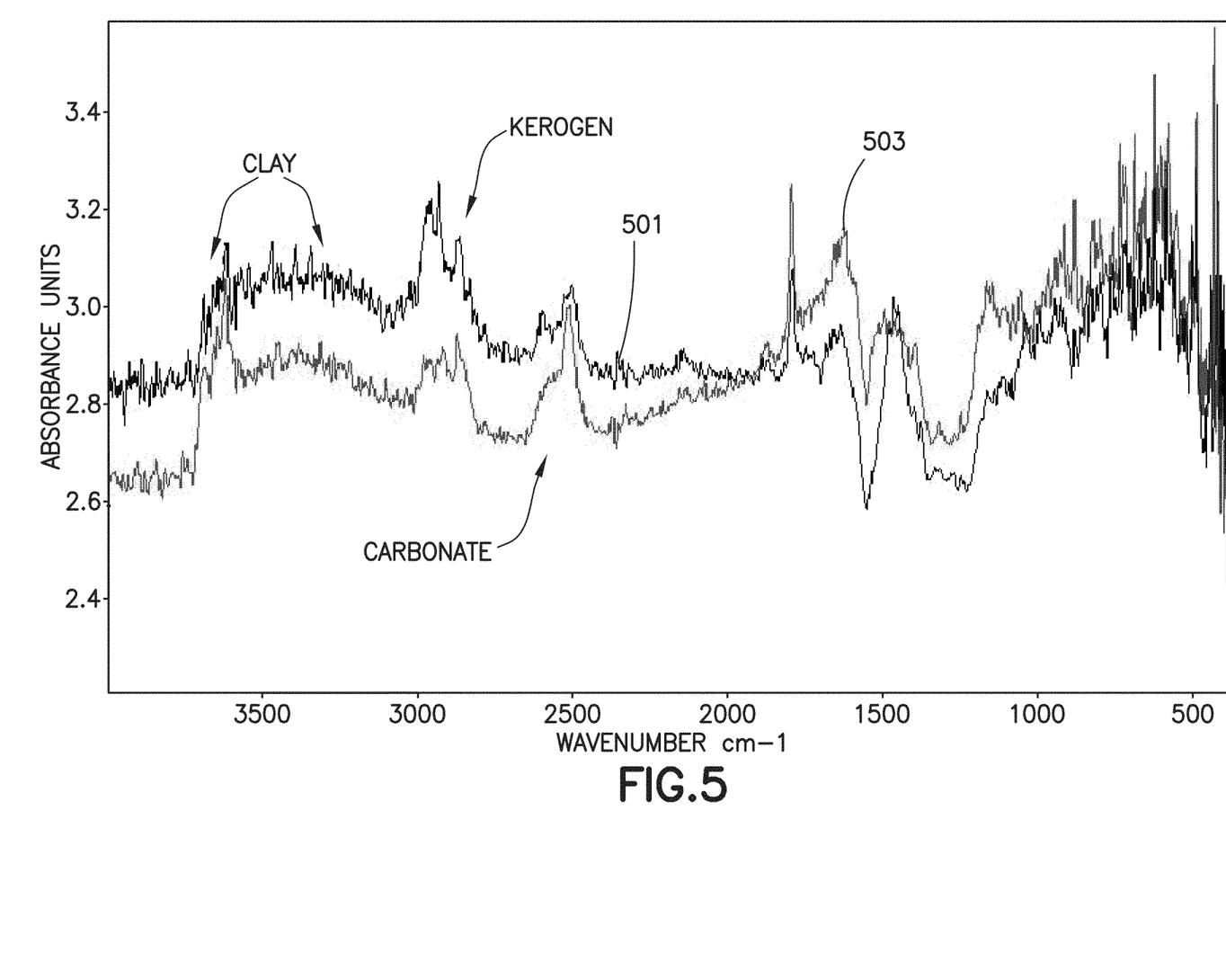
FIG. 5 is a graph of spectra according to embodiments of the subject disclosure.

FIG. 5 is a graph of DRIFTS spectra according to embodiments of the subject disclosure. These spectra show the major absorbance bands for clay, kerogen and carbonate from a cuttings sample as received (501) and after one cleaning step in soxhlet (503).

Figure 6:
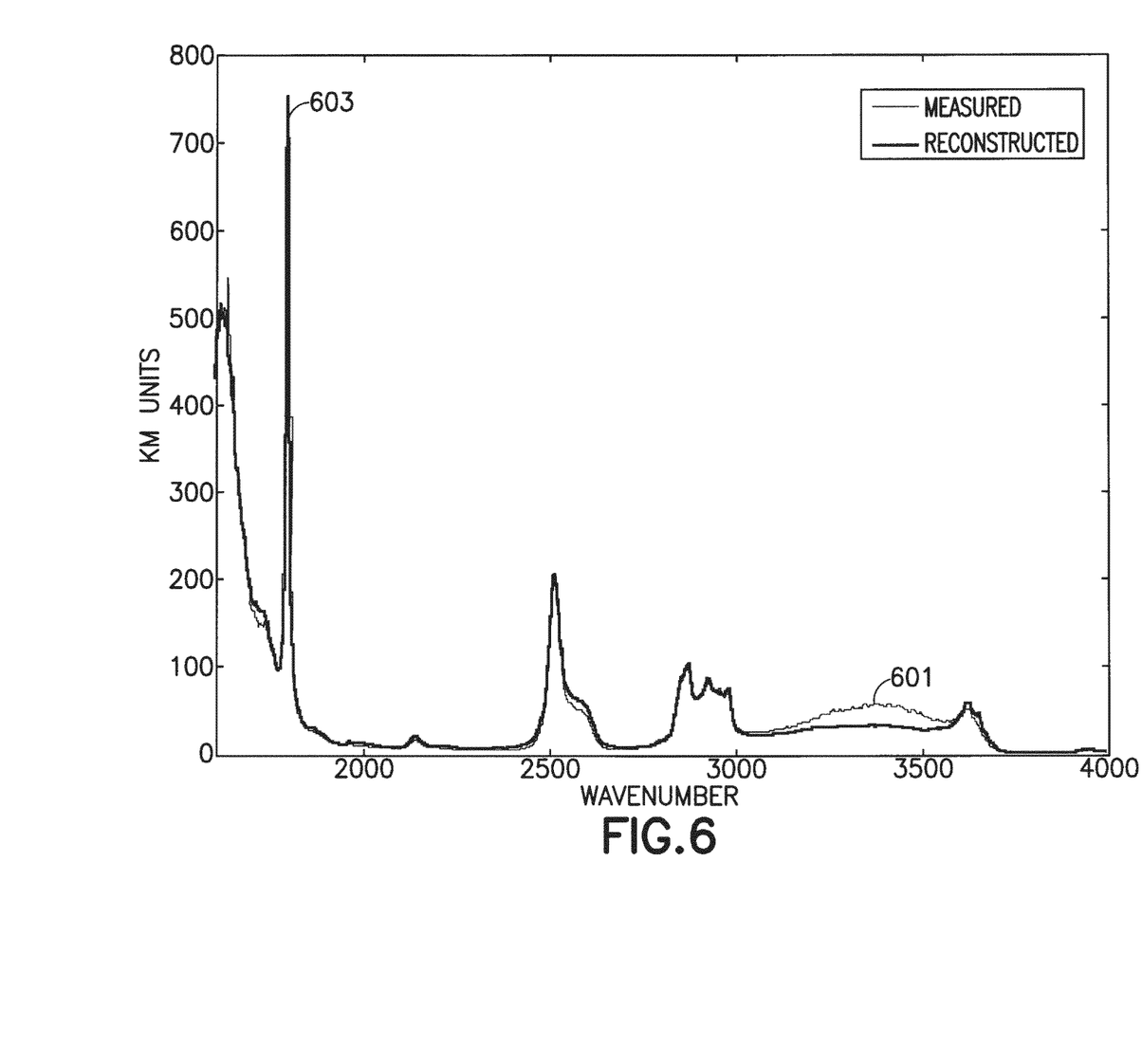
FIG. 6 illustrates a measured (601) Kubelka-Munk reflection spectrum on well-cuttings.

FIG. 6 depicts a measured (601) Kubelka-Munk reflection spectrum on well cuttings which were rinsed in diesel and pentane, crushed to less than 200 microns and rinsed again with pentane. The line (603) represents the reconstructed spectrum after a multiple linear regression was performed on a library of KM reflection spectra of mineral standards.

Figure 7:
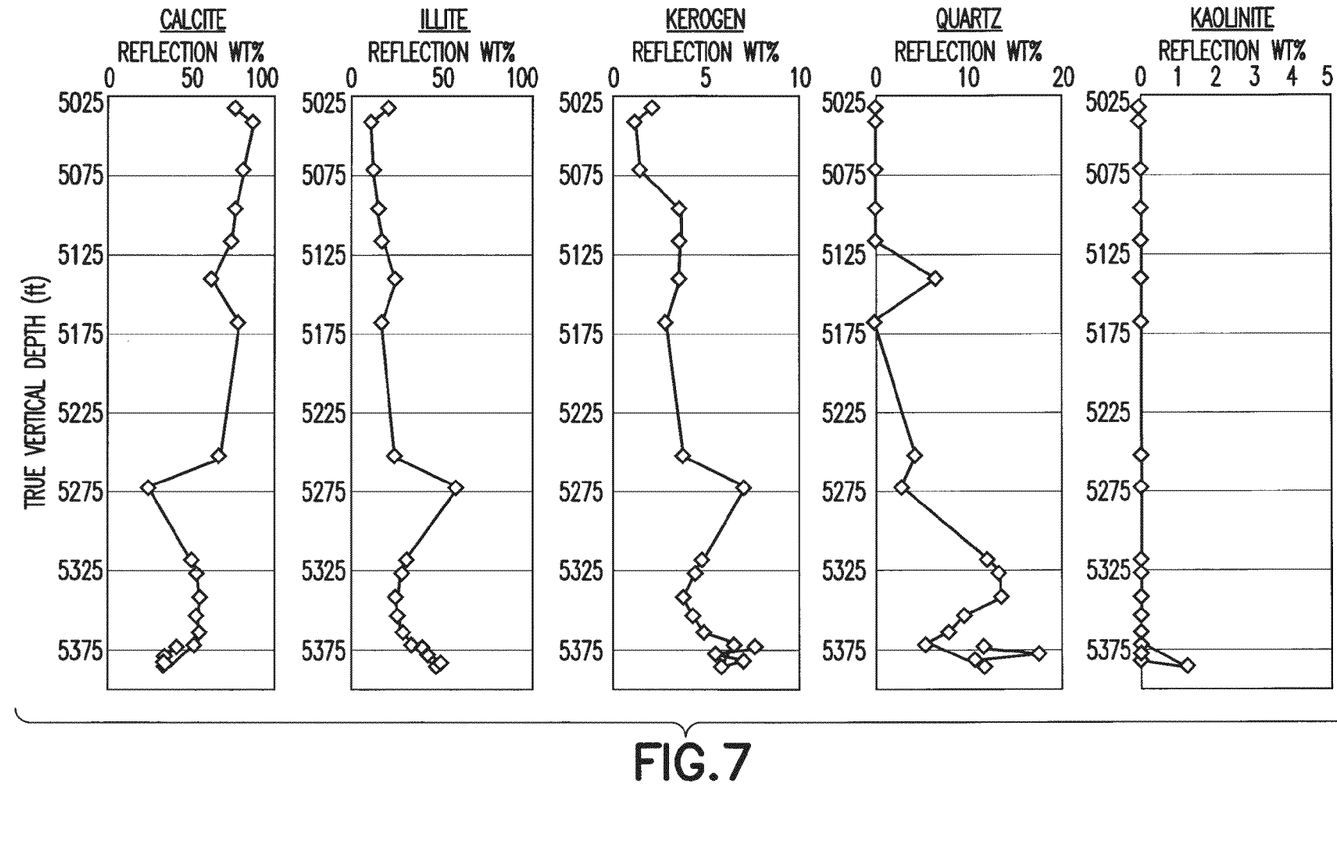
FIG. 7 illustrates a series of reflection mineral abundances on cuttings as a function of depth in a well.

FIG. 7 illustrates a series of reflection mineral abundances on cuttings as a function of depth in a well processed by cleaning, crushing, and weighted least squares regression on a library of mineral standards. As depicted one of the components is kerogen, not a true mineral, but with a detectable FT-IR signature. Plotting the data in this way allows one to see distinct changes in the formation lithology while traversing the well path. For example, at a vertical depth of 5275 ft, a formation boundary is crossed, becoming more clay rich, i.e., illite, with a significant decrease in carbonate, i.e., calcite. In addition to changes in the mineralogy, changes in the amount of kerogen can be detected with DRIFTS. FIG. 7 illustrates an increase in the amount of kerogen at a depth of 5275 ft, corresponding to the lithology change at this point.

Figure 8:
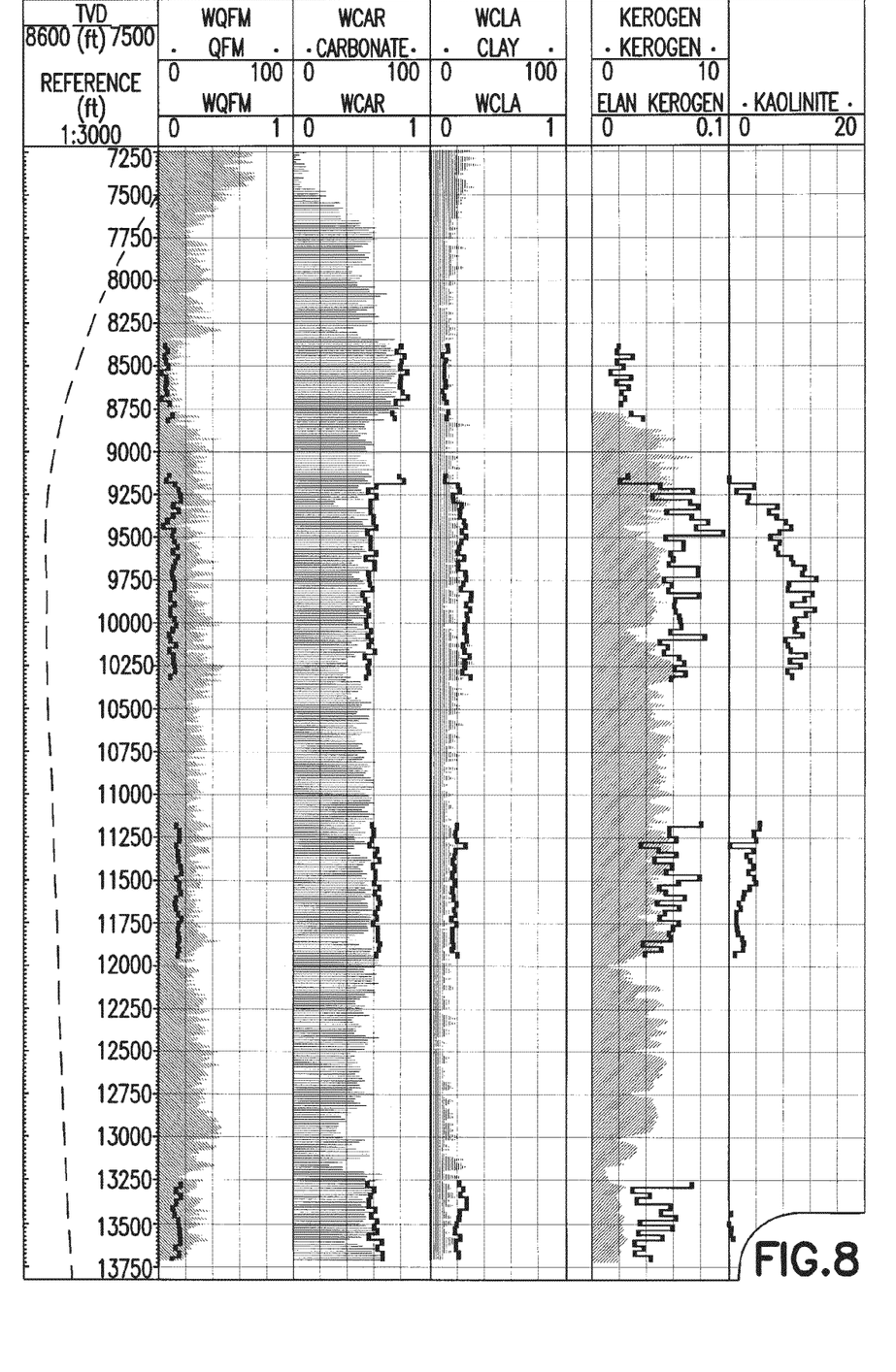
FIG. 8 illustrates reflection FT-IR analysis of cuttings.

FIG. 8 illustrates a log of three lithology columns and lithologies determined from cuttings in the well, i.e., no log data, depicted as bars. Three lithology columns are depicted in FIG. 8, WQFM (weight fraction of quartz, feldspar and mica), WCAR (weight fraction of carbonate minerals calcite plus dolomite), and WCLA (weight fraction of the sum of clay minerals illite, smectite, kaolinite and chlorite). The continuous log display of these lithologies is from the Spectrolith® processing of the EcoScope™ nuclear spectroscopy data. The bars in those tracks are lithologies determined from cuttings in the well, thus no log data. The cuttings were cleaned, crushed and reflection FT-IR was measured. Lithologies were then computed from the FT-IR spectra. An important point to consider is that if no log data is available you can come close to getting the lithology correct with the reflection FT-IR analysis of the cuttings. Similarly for kerogen, the bars are the kerogen from reflection FT-IR and have been shown to be accurate when compared to chemical analysis of the cuttings. Finally, there is another lithology track for cuttings analysis of kaolinite.

Figure 9:
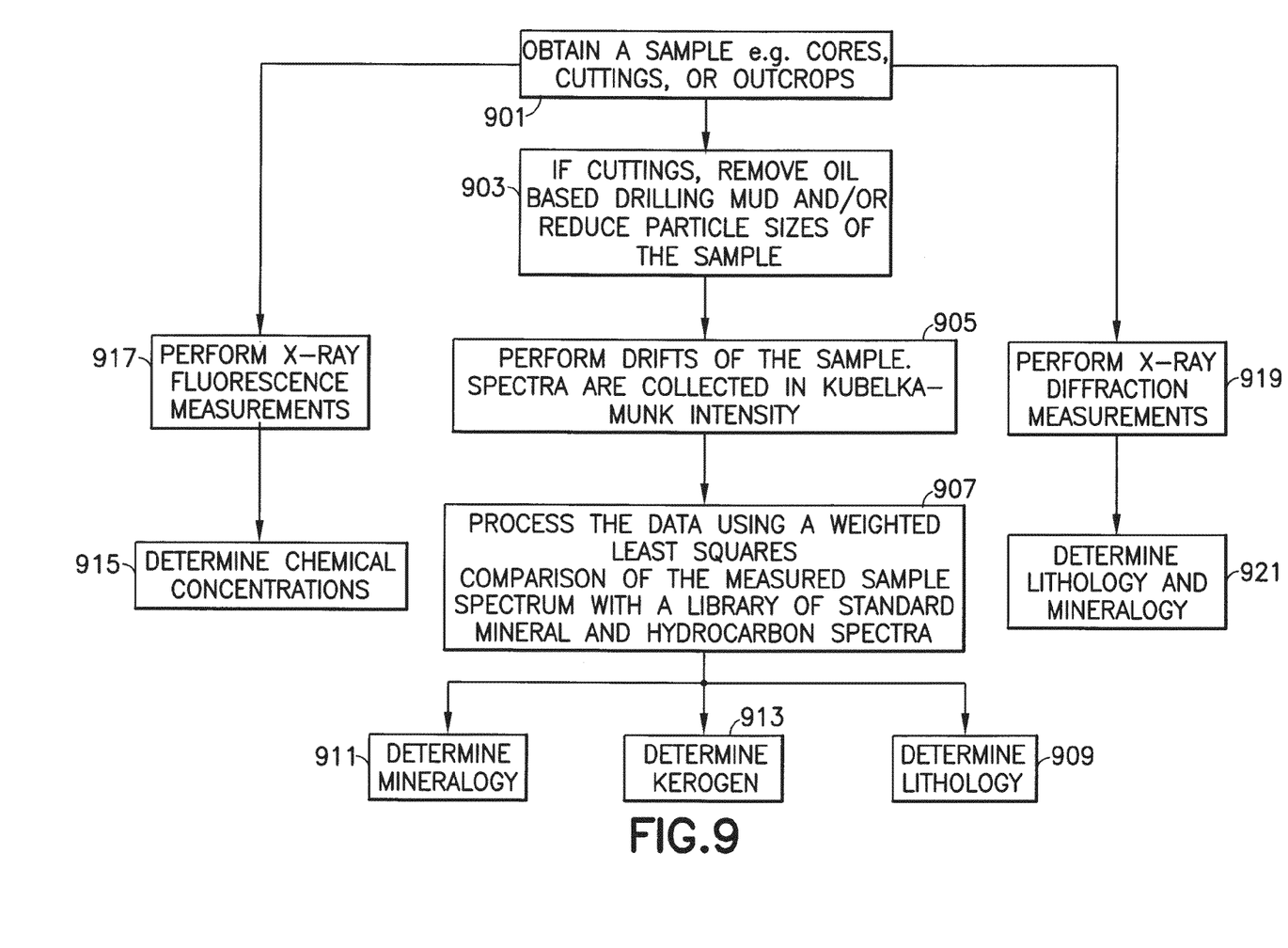
FIG. 9 is a flow chart illustrating steps in performing reflection FT-IR on earth materials.

FIG. 9 depicts a flow chart of embodiments of the subject disclosure. In an embodiment an earth sample is obtained (901) which in non-limiting examples may comprise cores, cuttings or outcrops. If the earth sample is cuttings (903), the cuttings may be cleaned to remove oil based drilling mud. The particle size of the cuttings may or may not be reduced. Diffuse Reflectance Infrared Fourier Transform Spectroscopy (DRIFTS) is performed on the earth sample (905) and the spectra are collected in Kubelka Munk intensity. The resulting data (907) is then processed using a weighted least squares comparison of the measured sample spectrum with a library of standard mineral and hydrocarbon spectra. From this processing, the mineralogy (911), kerogen content (913) and lithology (909) may be determined.

In embodiments, the sample (901) may be subjected to X-Ray fluorescence (917) and the chemical concentrations (915) of the sample determined. Finally, in embodiments, the sample (901) may be subjected to X-Ray diffraction (919) and the lithology and mineralogy (921) of the sample may be determined.

In embodiments, applications of the subject disclosure include using the chemistry for quality control. The measured mineralogy from DRIFTS would be used to compute the expected chemistry, and this would be compared to the measured chemistry from XRF. The compatibility of the chemistry and mineralogy data is checked by "reconstructing" the elemental concentrations from the mineralogy using a fixed element mineral matrix, details of which are disclosed in Herron et al. (See Herron et al., "Dual-Range FT-IR Mineralogy and the Analysis of Sedimentary Formations," 1997, Proceedings Paper No. SCA-9729, pp. 1-12), the contents of which are herein incorporated by reference. A comparison is then made between the reconstructed elemental concentrations from mineralogy to those measured by XRF.

In further embodiments, applications of the subject disclosure may include selecting a subset of mineral standards for which to analyze; for example, in carbonate settings it may not be necessary to analyze for multiple feldspar minerals, or the elemental concentrations may be used to determine rock classification and the anticipated formation mineralogy (See Herron et al., entitled "Geochemical Classification of Terrigenous Sands and Shales from Core or Log Data," Journal Sedimentary Petrology, Vol. 58, NO. 5, Pages 820-829, September 1988). In embodiments, the chemistry may be used to refine the mineralogy. For example, the carbonate minerals calcite ($CaCO_3$) and dolomite ($CaMg(CO_3)_2$) have similar FTIR spectra and can be difficult to quantitatively resolve on the basis of reflection FTIR alone, but they are easily discriminated by their Ca and Mg concentrations.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method of analyzing an earth sample taken from a borehole comprising:
   using a diffuse reflectance infrared Fourier transform spectrometer (DRIFTS) to:
      irradiate the earth sample with infrared energy;
      collect one or more spectra of the infrared energy reflected from the earth sample and creating a dataset therefrom;
   using one or more processing units to:
      analyze the dataset by performing regression analysis against a library of data obtained from standard spectra; and
      characterize the earth sample from results obtained by the regression analysis wherein the characterization includes determining an organic content of the earth sample.

2. The method of claim 1 wherein the characterization includes determining lithology, mineralogy and organic content of the earth sample.

3. The method of claim 1 wherein the earth sample is a core sample.

4. The method of claim 1 further comprising:
   obtaining the earth sample with limited or no sample preparation.

5. The method of claim 1 wherein the infrared radiation is in the mid-infrared range.

6. The method of claim 1 wherein the earth sample comprises drill cuttings.

7. The method of claim 6 further comprising:
   cleaning the drill cuttings to remove oil based mud; and
   crushing the drill cuttings to a particle size of less than 200 microns.

8. The method of claim 1 wherein the regression analysis uses a weighted least squares regression algorithm.

9. The method of claim 1 wherein the analyzing the dataset includes applying a Kubelka-Munk transformation to the collected one or more spectra.

10. The method of claim 1 wherein the standard spectra includes but is not limited to spectra for calcite, dolomite, illite, smectite, kaolinite and kerogen.

11. The method of claim 1 further comprising:
   obtaining a first chemical composition of the earth sample with an x-ray fluorescence (XRF) device; and
   comparing the first chemical composition to an expected chemical composition of the earth sample from the characterization of the earth sample.

12. The method of claim 1 further comprising:
   obtaining lithology and mineralogy data of the earth sample with an x-ray diffraction (XRD) device; and
   using the lithology and mineralogy data of the earth sample with the regression analysis to identify one or a plurality of mineral phases of the earth sample.

13. The method of claim 1 wherein the regression analysis is performed by an algorithm selected from a group consisting of multiple linear regression, weighed least squares regression or partial least squares regression.

14. An apparatus for analyzing an earth sample, comprising:
   an infrared light source for generating infrared energy at a plurality of wavelengths;
   a detector for detecting infrared energy that is reflected by the earth sample;
   an analyzer for analyzing the reflected energy by performing regression analysis against a library of data obtained from standard spectra; and
   determining an organic content of the earth sample from results obtained by the regression analysis.

15. The apparatus of claim 14 wherein the earth sample is a core sample.

16. The apparatus of claim 14 wherein the earth sample is obtained with limited or no sample preparation.

17. The apparatus of claim 14 wherein the infrared light source is in the mid-infrared range.

18. A method of characterizing an earth material using diffuse reflectance infrared Fourier transform spectroscopy comprising:
   obtaining drill cuttings from a selected region of a borehole;
   cleaning the drill cuttings to remove drilling mud;
   crushing the drill cuttings to a particle size of less than 200 microns;
   forming a sample with the crushed drill cuttings, wherein the sample is devoid of dilution solvent,
   with a radiation source illuminating the sample with infrared radiation;
   collecting and analyzing reflected diffuse energy from the sample; and
   characterizing the earth material by comparing the sample spectral response with those of known mineral standards using a regression analysis.

19. The method of claim 18 wherein the characterization includes determining lithology, mineralogy and organic content of the sample.

20. The method of claim 18, wherein illuminating the sample comprises illuminating a powder consisting of the crushed drill cuttings.

21. The method of claim 6, wherein irradiating the earth sample comprises irradiating a powder consisting of the crushed drill cuttings.

* * * * *